United States Patent [19]

Tapolczay et al.

[11] Patent Number: 4,857,551
[45] Date of Patent: Aug. 15, 1989

[54] INSECTICIDES

[75] Inventors: David J. Tapolczay, Bracknell; Mark A. Spinney, Workingham, United Kingdom

[73] Assignee: Imperial Chemical Industries PLC, London, United Kingdom

[21] Appl. No.: 90,930

[22] Filed: Aug. 31, 1987

[30] Foreign Application Priority Data

Sep. 15, 1986 [GB] United Kingdom ................ 8622296
Apr. 2, 1987 [GB] United Kingdom ................ 8707913

[51] Int. Cl.$^4$ ............................................. C07C 19/76
[52] U.S. Cl. ..................... 514/532; 514/568; 514/569; 560/60; 562/470
[58] Field of Search ............ 514/532, 568, 569; 560/060; 562/470

[56] References Cited

FOREIGN PATENT DOCUMENTS 0178823 4/1986 European Pat. Off. ............ 560/60

OTHER PUBLICATIONS

CA 101 (23): 211165z, Grohe (German Offen. DE 3248507-5, Jul. 1984.
CA 105 (9): 78670z, Bushell, EPA EP 178926 A2, 23 Apr. 1986.
CA 100 (13) 103362g, Heubach, G et al., Ger. Offen. DE 3221915 A1, 15 Dec. 1983.

*Primary Examiner*—Paul J. Killos
*Attorney, Agent, or Firm*—Cushman, Darby & Cushman

[57] ABSTRACT

A method of killing or controlling insect, mite or nematode pests which method comprises applying to the insect or to the locus thereof an effective amount of a compound of the formula (I):

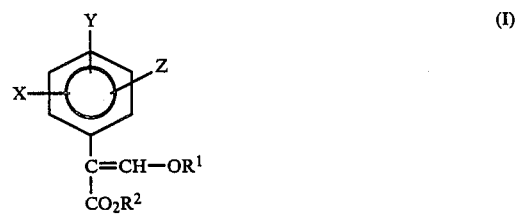

wherein R is hydrogen or $C_{1-4}$ alkyl; and X, Y and Z are independently selected from hydrogen, halogen, or $OR^1$ where $R^1$ is optionally substituted aryl or heteroaryl group. Certain of the compounds are new.

8 Claims, No Drawings

INSECTICIDES

The present invention relates to a method of killing or controlling insect, mite or nematode pests and to certain compounds for use in that method.

Published European Patent Application No. 178,826A describes a group of acrylic acid derivatives useful as fungicides.

The applicants have found that certain of these compounds have useful insecticidal/nematocidal activity. In addition the compounds may have knockdown activity against flies and mosquitoes.

According to the present invention there is provided a method of killing or controlling insect, mite or nematode pests which method comprises applying to the pest or to the locus thereof an effective amount of a compound of formula (I)

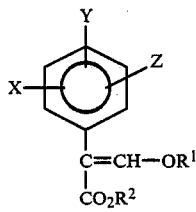
(I)

wherein $R^1$ and $R^2$ are independently selected from hydrogen and $C_{1-4}$ alkyl; and X, Y and Z are independently selected from hydrogen, halogen, or $OR^3$ where $R^3$ is an optionally substituted aryl group.

As used herein the term "aryl" includes phenyl.

Suitable optional substituents for aryl groups include haloalkyl wherein the alkyl portion suitably contains from 1 to 6 carbon atoms, and the halo atom(s) are suitably selected from fluorine, chlorine and bromine. A particular example of a haloalkyl substituent is trifluoromethyl.

Examples of $R^1$ groups are methyl and ethyl.

Examples of $R^2$ groups are methyl and iso-propyl.

Examples of halogen groups X, Y and Z include chlorine and bromine.

Suitably at least one of X, Y and Z is hydrogen.

When X, Y and Z are other than hydrogen, they are preferably situated at the 2,4 and 6 positions of the phenyl ring.

When one of X, Y and Z is hydrogen, the other two substituents are preferably at the 2,4 positions on the phenyl ring.

When only one of X, Y and Z is other than hydrogen, it is suitably located at the 2 position on the phenyl ring.

Compounds of formula (I) contain a double bond and therefore exist in cis or trans- isomeric forms. The invention covers mixtures of these isomers in all proportions.

Preferably the compound of formula (I) is in the form of the E (trans) isomer.

Examples of compounds of formula (I) are set out in Table I below.

TABLE I

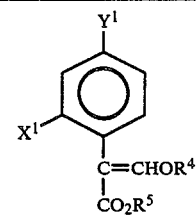

| COMPOUND NO | $X^1$ | $Y^1$ | $R^4$ | $R^5$ | ISOMER |
|---|---|---|---|---|---|
| 1 | Cl | Cl | $CH_3$ | $CH_3$ | E |
| 2 | Cl | Cl | $CH_2CH_3$ | $CH_3$ | E |
| 3 | Cl | Cl | $-CH(CH_3)_2$ | $CH_2CH_3$ | E |
| 4 | Cl | Cl | $CH(CH_3)_2$ | $-CH_3$ | E |
| 5 | Br | Br | H | $CH_3$ | E |
| 6 | Br | Br | $CH_3$ | $CH_3$ | E |
| 7 | Br | Cl | $CH_3$ | $CH_3$ | E |

In so far as some of the compounds of formula (I) are not exemplified in EP-A-No. 178826, they are novel and as such form an aspect of the invention.

In particular according to the invention there is provided a compound of formula (IA)

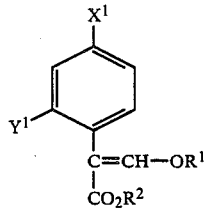
(IA)

wherein $X^1$ and $Y^1$ are halogen and $R^1$ and $R^2$ are as defined in relation to formula (I), provided that when $X^1$ and $Y^1$ are chlorine, $R^1$ or $R^2$ is other than methyl.

The compounds of formula (I) can be prepared as described in EP No. 0178826 A.

One particularly useful route for the preparation of compounds of formula (I) is set out in Scheme II of EP-A-No. 0178826.

A compound of formula (II):

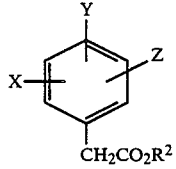
(II)

wherein $R^2$, X, Y and Z are as hereinbefore defined in relation to formula (I); is reacted with a formate ester, for example of formula $HCO_2R^6$ where $R^6$ is $C_{1-6}$ alkyl such as methyl, in the presence of a base, to give a compound of formula (I) wherein $R^1$ is hydrogen.

The reaction is suitably carried out in an inert organic solvent such as dimethyl formamide. Preferably a strong base such as sodium hydride is employed.

Compounds of formula (I) wherein $R^1$ is hydrogen can be converted to compounds wherein $R^1$ is $C_{1-4}$ alkyl by conventional etherfication techniques. The compounds may be reacted with an etherifying agent of formula (III)

$$R^7-Q \qquad (III)$$

wherein $R^7$ is $C_{1-4}$ alkyl and Q is a leaving group.

Examples of suitable leaving groups Q include halogen such as bromine or iodine, preferably iodine.

The etherfication reaction is suitably carried out in an inert organic solvent such as dimethylformamide in the presence of a base such as potassium carbonate.

Compounds of formula (II) are either known compounds or they can be prepared from known compounds by conventional methods. For instance, compounds of formula (II) can be prepared in accordance with Scheme A below.

SCHEME A

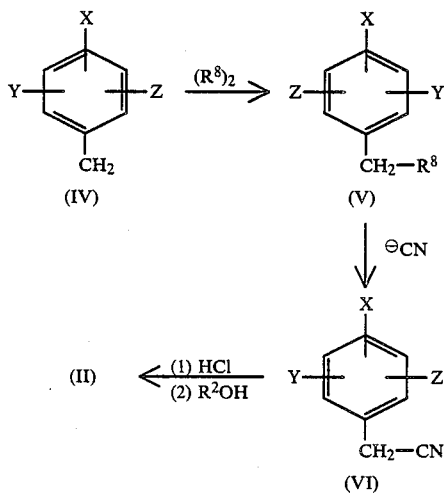

wherein $R^2$, X, Y and Z are as defined in relation to formula (I) and $R^8$ is halogen in particular bromine.

Suitable reaction conditions for each stage in Scheme A will be readily determinable. Specific conditions are illustrated in Preparations 1–4 hereinafter.

Compounds of formula (IV) are either known compounds or they can be prepared from known compounds by conventional methods. For example, by halogenation of an appropriate toluene derivative.

The E-isomer of the compound of formula (I) may be obtained by conventional separation techniques such as column chromatography.

In order to apply the compounds to the locus of the pests they are usually formulated into compositions which include in addition to the insecticidally active ingredient or ingredients of formula (I), suitable inert diluent or carrier materials, and/or surface active agents. The compositions may also comprise another pesticidal material, for example another insecticide, nematocide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triiso-propylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain from 5.95% suitably from 10–85% by weight of the active ingredient or ingredients. When diluted to form aqueous preparations such preparations may contain varying amounts of the active ingredient depending upon the purpose for which they are to be used. For agricultural, horticultural or domestic purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The above described compositions are active against a range of pests including nematodes.

Rates of application will depend upon a number of factors including the type of pest, degree of infestation etc. However in general application of from 0.5 to 4.0 Kg/ha will be appropriate.

The following Examples illustrate the invention.

EXAMPLE 1

This Example illustrates the preparation of Compound No. 2 in Table I.

To a stirred solution of methyl-2-(2,4-dichlorophenyl)-3-hydroxypropenoate (1.2 g) (prepared by esterification of 2,4-dichlorophenylacetic acid and reaction of the product with methyl formate using a method analogous to that described in Example 4 of EP-A-No. 0178826) in dimethylformamide (20 ml), was added potassium carbonate (excess) and ethyl iodide (0.5 mls) at room temperature. The solution was stirred for 2 hours and then the reaction mixture was poured into water (50 ml), and the product extracted into ether (3×80 mls). The combined ether extracts were washed with water (2×50 ml), dried over magnesium sulphate and concentrated to an oil. Column chromatography of the oil using 70:30 petrol:diethyl ether gave the Compound 1 in Table I in pure form (1.26 g, 93%). (Structure confirmed by n.m.r., i.r. and mass spectroscopy).

EXAMPLE 2

Compounds 1, 3 and 4 of Table I were obtained by analgous methods to those described in Example 1 above.

Preparation 1

Bromine (0.82 ml) in carbontetrachloride (20 ml) was added dropwise to a stirred solution of 4-bromotoluene (2.5 g) in carbontetrachloride (30 ml) over a period of 1 hour. The reaction mixture was stirred in the dark, overnight, then deaerated and the solvent evaporated. The product was purified by Kughelrohr distillation at 0.5 mm Hg pressure, the desired 2,4-dibromotoluene being collected at 60°-70° C. (yield 2.55 g, 70%).

2-Bromo-4-chlorotoluene was prepared in an analogous manner using 4-chlorotoluene as the starting material

Preparation 2

To a stirred solution of 2-bromo-4-chlorotoluene (2.0 g) in carbontetrachloride (50 ml) under reflux, was added dropwise a solution of bromine (0.722 ml) in carbontetrachloride (10 ml). The reaction mixture was heated under reflux for 3 hours whilst illuminating with a 250 w lamp. The solvent was then evaporated under reduced pressure and the products separated by Kughelrohr distillation at 0.5 mm Hg pressure, the desired fraction coming over at 100° C. After further purification using column chromatography (silica column with petrol eluent) the desired product

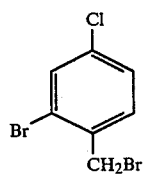

(i)

was obtained as a colourless oil.

The dibromo analogue

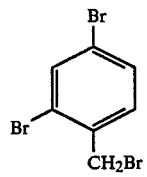

(ii)

was obtained by an analogous process, using 2,4-dibromotoluene from Preparation 1 as the starting material.

Preparation 3

To a stirred solution of compound (ii) (2.5 g) from Preparation 2 in ethanol (20 ml) and water (2 ml) at room temperature was added sodium cyanide (0.5 g). The reaction mixture was heated under reflux for 4 hours and then the solvent removed under reduced pressure. The residue was extracted into ethyl acetate (3×50 ml) and water (2×50 ml). The organic layer was separated, dried over magnesium sulphate and the solvent removed. After recrystallisation the desired product

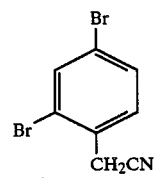

(iii)

was obtained (1.7 g).

By an analogous method, the compound

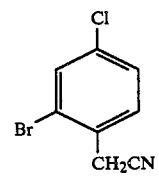

(iv)

was obtained from compound (i) from Preparation 2.

Preparation 4

Compound (iv) Preparation 3 (1.0 g) was added to concentrated hydrochloric acid (15 ml) and the mixture stirred at 40° C. for one hour. After that time the temperature was raised to reflux temperature (100° C.) and methanol (10 ml) was added. Reflux was continued for two hours and then the reaction was quenched using iced water. After extraction into diethyl ether the desired methyl (2,4-dibromophenyl)acetate was obtained.

Methyl (2-bromo-4-chlorophenyl) acetate was obtained from compound (iv) from Preparation 3 in an anolgous manner.

EXAMPLE 3

This Example illustrates the preparation of Compounds 5 and 6 in Table I.

Methyl (2,4-dibromophenyl) acetate was reacted with sodium hydride in dry dimethylformamide in a manner analogous to that described in Example 4 of EP-A-No. 0178826 to obtain Compound 5 in Table I as an oil (structure confirmed by n.m.r., i.r. and MS).

Reaction of Compound 5 (1 g) with methyl iodide (1 ml) in the presence of an excess of potassium carbonate in a manner anologous to that described above in Example 1.

EXAMPLE 4

Compound 7 in Table I was obtained from methyl (2-bromo-4-chlorophenyl) acetate from Preparation 4 above using methods analogous to those described in Example 3.

Biological Data

The insecticidal properties of the Compound of the formula (I) were demonstrated as follows:

The activity of the compound was determined using a variety of insect, mite and nematode pests. The compound was used in the form of liquid preparations containing from 100 to 500 parts per million (ppm) by weight of the compound. The preparations were made by dissolving the compound in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

The results of the tests are given in Table VII for each of the products, at the rate in parts per million given in the second column as a grading of mortality designated as 9, 5 or 0 wherein 9 indicates 8-100% mortality (70-100% root-knot reduction as compared with untreated plants for *Meloidogyne incognita*), 5 indicates 50-79% mortality (50-69% root-knot reduction for *Meloidogyne incognita*).

In Table VII the pest organism used in designated by a letter code and the pest species, the support medium or food, and the type and duration of test is given in Table VI.

TABLE VI

| CODE LETTERS (Table IV) | TEST SPECIES | SUPPORT MEDIUM/FOOD | TYPE OF TEST | DURATION (days) |
| --- | --- | --- | --- | --- |
| Tua | *Tetranychus urticae* (spider mites - adults) | French bean leaf | Contact | 3 |
| Tue | *Tetranychus urticae* (spider mites - ova) | French bean leaf | Contact | 6 |
| MP | *Myzus persicae* (aphids) | Chinese Cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Plastic pot | Contact | 1 |
| SP | *Spodoptera exigua* (lesser army worm - larvae) | Cotton leaf | Residual | 3 |
| MI | *Meloidogyne incognita* (tomato root-knot eelworm - larvae) | Semi in-vitro | Residual | 7 |

"Contact" test indicates that both pests and medium were treated and "Residual" indicates that the medium was treated before infestation with the pests.

TABLE VII

| COMPOUND NO. | RATE (ppm) | Tua | Tue | MP | NL | MD | BG | HV | SP | DB | MI |
| --- | --- | --- | --- | --- | --- | --- | --- | --- | --- | --- | --- |
| 1 | 500 | 9 | 5 | 0 | 5 | 9 | 5 | — | — | 9 | — |
| 2 | 500 | 0 | 0 | 0 | 0 | 0 | 5 | 0 | — | 9 | — |
| 3 | 500 | 0 | 0 | 0 | 0 | 0 | 0 | 0 | 0 | 9 | — |
| 4 | 500 | 0 | 0 | 0 | 0 | 0 | 0 | 0 | 0 | 9 | — |
|  | 250 | — | — | — | — | — | — | — | — | — | 5 |
| 5 | 500 | 0 | 0 | 0 | 0 | 0 | 0 | 0 | 0 | 9 | — |
|  | 250 | — | — | — | — | — | — | — | — | — | 9 |
| 6 | 500 | 9 | 9 | 0 | 9 | 0 | 0 | 0 | 0 | 9 | — |
| 7 | 500 | 9 | 0 | 0 | 9 | 5 | 5 | 0 | 0 | 9 | — |
|  | 250 | — | — | — | — | — | — | — | — | — | 5 |

The knockdown properties of Compound 1 in Table I against *Musca domestica* were demonstrated using a Kearns and March test as follows.

A sample of Compound 1 was diluted in acetone to give a 10,000 ppm solution (1 ml) was then sprayed into an observation chamber containing twenty female houseflies over a 3 second period. Regular assessments of knockdown were then taken up to 10 minutes after applications from which KT 50 and 90 values were calculated.

Compound 1 in Table I under these conditions showed a KT 50 of 4.7 minutes and a KT 90 of 7.3 minutes.

We claim:

1. A method of killing or controlling insect, mite or nematode pests which method comprises applying to the pest or to the locus thereof an effective amount of a compound of formula (I):

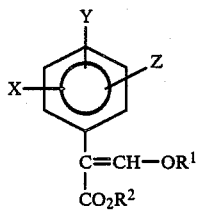

(I)

wherein $R^1$ and $R^2$ are independently selected from hydrogen and $C_{1-4}$ alkyl; and X, Y and Z are independently selected from hydrogen, halogen, or $OR^3$ where $R^3$ is an optionally substituted aryl group.

2. A method according to claim 1 wherein X, Y and Z are at the 2,4 and 6 positions on the ring.

3. A method according to claim 1 or claim 2 wherein one of X, Y and Z is hydrogen.

4. A method according to claims 1–3 wherein the compound of formula (I) is in the form of the E (trans) isomer.

5. A method according to claims 1–4 wherein $R^1$ is methyl or ethyl.

6. A method according to claim 5 wherein $R^2$ is methyl or iso-propyl.

7. An insecticidal, miticidal or namaticidal composition for use in a method according to claim 1 and comprising an insecticidally effective amount of a compound of formula (I)

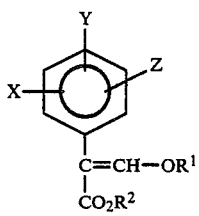

(I)

wherein $R^1$ and $R^2$ are independently selected from hydrogen and $C_{1-4}$ alkyl; and X, Y and Z are independently selected form hydrogen, halogen or $OR^3$ where $R^3$ is an optionally substituted aryl group, in combination with a carrier or diluent.

8. An insecticidal, miticidal or nematicidal composition, for use in a method according to claim 1, and comprising a compound of formula (1A)

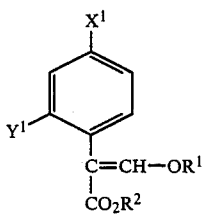

(IA)

wherein $X^1$ and $Y^1$ are halogen, $R^1$ is methyl, ethyl and isopropyl and $R^2$ is as defined in claim 1 provided that when $X^1$ and $Y^1$ are chlorine, $R^1$ or $R^2$ is other than methyl, in combination with a diluent or carrier.

* * * * *